United States Patent [19]

Regan et al.

[11] 4,325,697

[45] Apr. 20, 1982

[54] METHOD AND APPARATUS FOR MEASURING HAND-EYE COORDINATION WHILE TRACKING A CHANGING SIZE IMAGE

[75] Inventors: David M. Regan; Kenneth I. Beverley, both of Halifax, Canada

[73] Assignee: The United States of America as represented by the Secretary of the Air Force, Washington, D.C.

[21] Appl. No.: 193,048

[22] Filed: Oct. 2, 1980

[51] Int. Cl.³ .............................................. G09B 5/00
[52] U.S. Cl. .................................................. 434/258
[58] Field of Search .......... 434/258; 273/1 GC, 1 GE

[56] References Cited

U.S. PATENT DOCUMENTS

| | | | |
|---|---|---|---|
| 3,357,115 | 12/1967 | Kelley | 434/258 |
| 3,483,302 | 12/1969 | Ashkenas et al. | 434/258 |
| 3,579,865 | 5/1971 | Walker | 434/258 |
| 3,971,143 | 7/1976 | Slomski | 434/258 |
| 4,028,819 | 6/1977 | Walker | 434/258 |
| 4,169,592 | 10/1979 | Hall | 434/258 X |

Primary Examiner—William H. Grieb
Attorney, Agent, or Firm—Donald J. Singer; Willard R. Matthews

[57] ABSTRACT

Hand-eye coordination while tracking a changing size image is measured by a method that includes: displaying an image that is varied in size in response to a programmed signal; having the person under test manipulate a manual control that effects image size change by cancelling the effects of the programmed signal; and, comparing the tracking response with the image size change, the difference therebetween being a measure of the subjects' hand-eye coordination. The image can be randomly displaced laterally during test and its light intensity parameters can be varied. Image size change is programmed in various ways including randomly occurring reversals in direction of change. The method is implemented by means of an image figure generator that provides a rectangular image on the screen of a CRT. A programmable image size change circuit controls the size of the rectangle in concert with a potentiometer circuit that is manually controlled by the test subject. Other electronic circuits provide for lateral displacement of the image, image/screen intensity changes and the processing and display of tracking errors.

19 Claims, 28 Drawing Figures

METHOD AND APPARATUS FOR MEASURING HAND-EYE COORDINATION WHILE TRACKING A CHANGING SIZE IMAGE

STATEMENT OF GOVERNMENT INTEREST

The invention described herein may be manufactured and used by or for the Government for governmental purposes without the payment of any royalty thereon.

BACKGROUND OF THE INVENTION

This invention relates to a procedure for quantifying a person's ability to track changes in size and in particular to a method and apparatus for testing eye-hand coordination in tracking a changing-size image in the presence of various visual perturbations.

Psychophysical evidence supports the idea that the human visual pathway computes an object's rate of change of angular size rather independently of the object's trajectory and rather independently of other visual parameters including contrast and intensity. This independence can provide a basis for accurately judging the component of an object's velocity along a line through the eye in the working visual environment where many visual parameters vary simultaneously, and data acquired using such a basis can be very useful in predicting a subject's performance in tasks of eye-limb coordination, especially where visual information is largely restricted to the changing-size channel.

A review of the state-of-the-art reveals that there has been reported evidence that the visual pathway processes motion-in-depth information in several channels that are, to a first approximation, independent of each other. These include channels sensitive to changing size and channels sensitive to the relative velocities of the retinal images.

The defining property of a channel is that it is sensitive to one feature of the stimulus while being comparatively insensitive to all other features of the stimulus. There is one clear advantage for an organism of processing a visual system that operates as though composed of channels: in the complex, everyday visual world a channel would respond to one particular stimulus feature, unperturbed by all other accompanying visual stimuli. Thus, channel operation might go some way to explaining the notable reliability of eye-limb coordination exhibited by skilled individuals such as airplane pilots.

There are several flying tasks in which the pilot must accurately control his distance from an object in the face both of continuous perturbations of position in three dimensions, and of continuous perturbations of light intensity. It is proposed that the changing-size channels might be involved in the performance of such tasks.

Suppose, for example, that a pilot's task is to maintain a constant distance from a second airplane. If he starts to move closer, parts of the second airplane (e.g., rivets, identification markings) will appear to grow progressively larger at a rate determined by the speed with which he is approaching the other airplane. It is proposed that the changing-size channel is directly sensitive to the rate of change of size and, furthermore, it has been demonstrated that the changing-size channel is comparatively insensitive to sideways motion and to flicker. Thus, the changing-size channel could provide the pilot with a basis for reliably detecting his approach to the other airplane, even when there is appreciable sideways motion relative to the other airplane, and even when light intensity is fluctuating due, for example, to changes in his attitude relative to the sun. By reliably signalling "slowly approaching", and "slowly moving away" the changing-size channel could aid the pilot to successfully "hunt" around the desired distance from the other airplane.

In the past conventional psychophysical methods have been used to measure visual sensitivity to changing-size and to investigate the dynamic properties of the changing-size channel. However, it is not necessarily true that conventional psychophysical measurements of detection sensitivity will reliably predict an individual's performance of a task that demands skilled eye-limb coordination. For example, even if it is the case that the changing-size channel is important in formation flying, previous psychophysical measurements of changing-size sensitivity need not necessarily predict the accuracy with which a pilot can maintain distance from a second airplane, since the previous psychophysical measurements were restricted to simple visual detection sensitivity, threshold elevation and aftereffect strength: thus, in previous experiments, it was not required that subjects use changing-size information to perform a demanding task of eye-limb coordination.

In accordance with the foregoing it is seen that there currently exists the need for procedures and devices adapted to measure the precision with which a subject tracks a changing-size stimulus, and in particular to assess the subject's eye-hand coordination when the stimulus is processed by his changing-size channel alone. Furthermore, when flying an airplane or helicopter the pilot's changing-size channel must operate reliably even when the changing-size stimulus is accompanied by fluctuations of brightness and varying sideways motion. Therefore, it is also desirable that in the testing procedures the changing-size tracking stimulus can be accompanied by correlated or uncorrelated flicker and/or sideways motion. The present invention is directed toward providing a method and apparatus that will accomplish these ends.

SUMMARY OF THE INVENTION

The invention is directed to a method and apparatus for measuring precision of hand-eye coordination by quantifying a subject's ability to track changes in size. An image size tracking device is provided in which a rectangle is generated on a CRT screen by a rectangle generator comprising X and Y raster generators. The size and position of the rectangle on the screen are controlled by various input sources including pseudo random sequence bit noise generators; a preset-frequency sine, square, or triangle wave oscillator; irregular velocity reversers; and an operator controlled potentiometer. An error analyzer having an RMS stage and an integrator is used to integrate errors over a period of time. The output from the error analyzer is displayed on digital voltmeters.

It is a principal object of the invention to provide a new and improved method for testing a subject for hand-eye coordination while tracking a changing size image.

It is another object of the invention to provide apparatus for testing a subject for hand-eye coordination while tracking a changing size image.

It is another object of the invention to provide apparatus for quantifying a person's ability to track changes in size of an image.

It is another object of the invention to provide apparatus for measuring a person's hand-eye coordination while tracking a changing size image that includes means for introducing correlated or uncorrelated flicker and/or lateral motion of the image being tracked.

These, together with other objects, features and advantages of the invention will become more readily apparent from the following detailed description when taken in conjunction with the illustrative embodiment of the accompanying drawings.

DESCRIPTION OF THE DRAWINGS

FIG. 2 is a time interval histogram of durations between successive reversals of the changing size tracking stimulus of FIG. 1a;

DETAILED DESCRIPTION OF THE PREFERRED EMBODIMENT

The invention comprehends a method and implementing apparatus for measuring a subject's hand-eye coordination while tracking a changing-size image. The apparatus of the invention can measure tracking errors in the special case that the subject's visual information for tracking is restricted to the changing-size channel. There also is provision for adding perturbing signals and assessing their effects on tracking errors.

Figure 4:
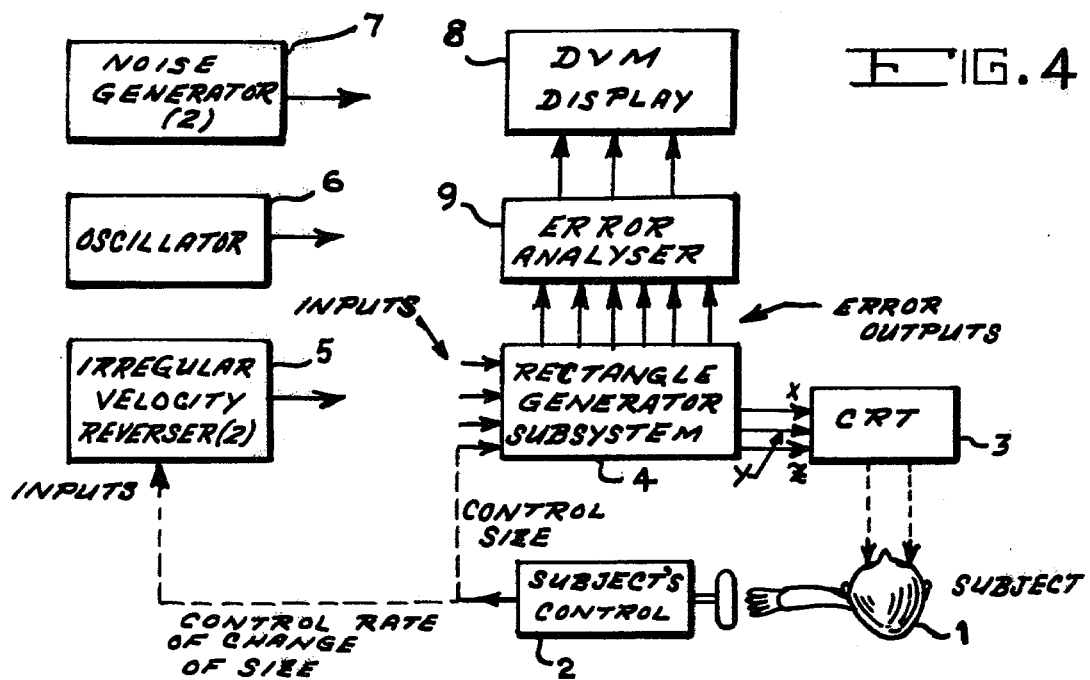
FIG. 4 is a functional block diagram of the tracking apparatus of the invention.

A functional block diagram of the apparatus of the invention is shown by FIG. 4. This comprises a cathode ray tube (CRT) 3, the screen of which is viewed by the subject under test 1. A changing-size image is developed for the screen of CRT 3 by means of rectangle generator subsystem 4 and the control circuits represented by noise generator 7, oscillator 6 and irregular velocity reverser 5. The subject under test 1 attempts to override the image size control of these circuits by manually manipulating subject's control 2. His success in accomplishing this is determined by error analyzer 9 and the results are displayed by digital voltmeter displays 8.

In practicing the method of the invention an image is displayed on a screen in view of the subject being tested. The image is varied in accordance with any of a number of pre-selected programmed ways. The subject under test tracks the image change by attempting to cancel any variation thereof by means of a hand manipulated potentiometer circuit. The difference between the subjects tracking response and the actual image size change is detected as a measure of hand-eye coordination in tracking the image change. Other steps of the method include randomly laterally displacing the image during test and varying the light intensity of the image relative to the screen.

Figure 1A:
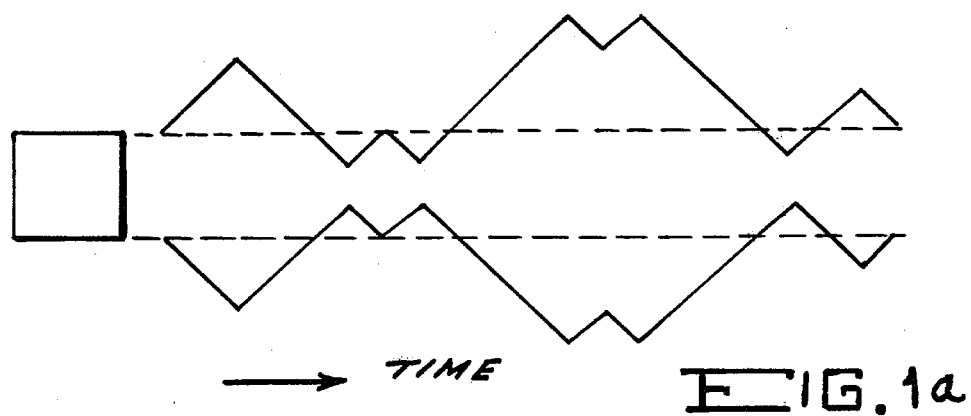
FIG. 1a diagrammatically illustrates constant velocity variations in size (antiphase tracking stimulus) of an image used in practicing the method of the invention.
Figure 2:
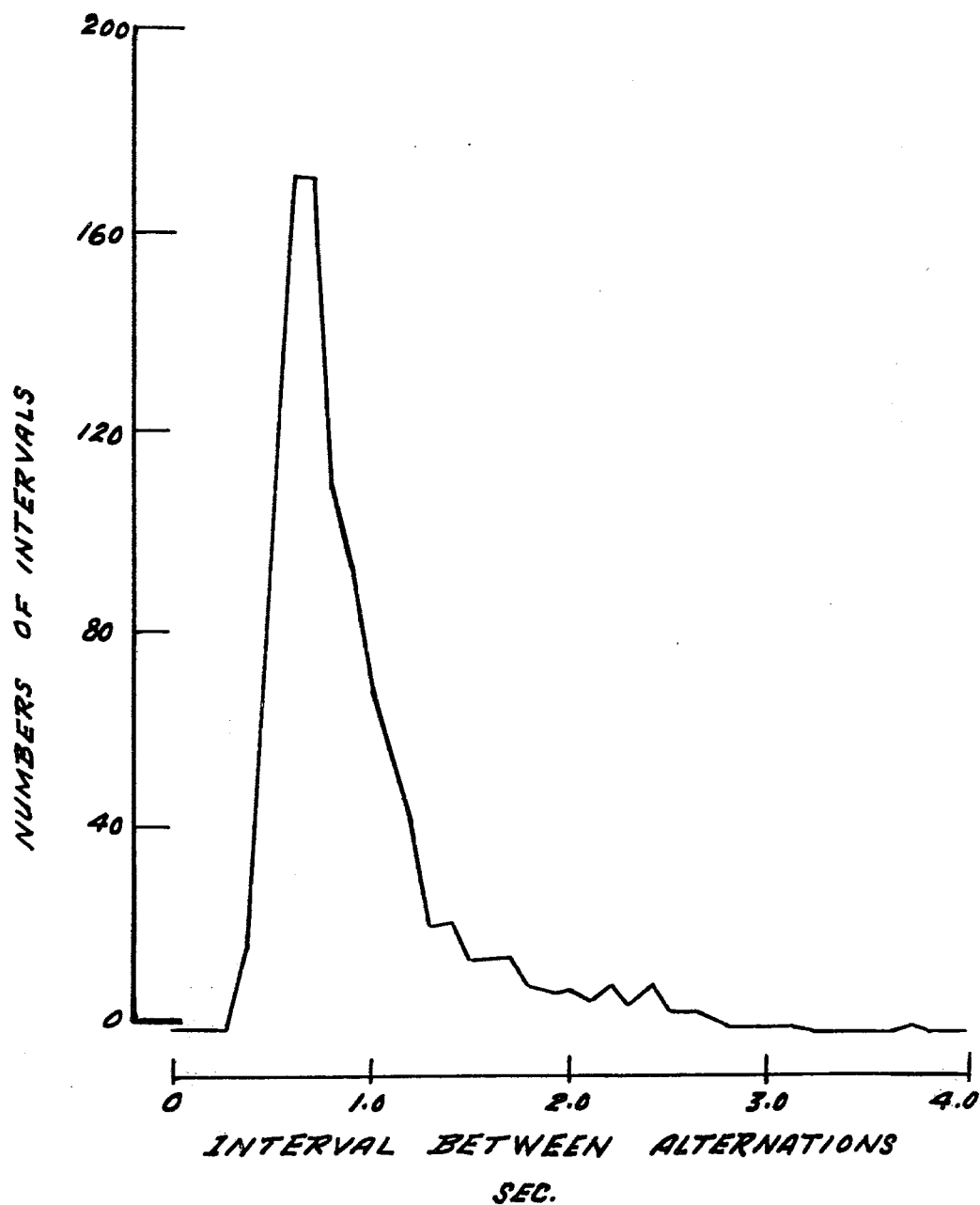

By way of example a subject was tested using the above procedures and various modes of operation. Initially the test consisted of tracking a constant rate of change of size. In this approach the subject viewed a bright stimulus square displayed on a CRT. The square's luminance was 5 cd m$^{-2}$ and its mean side length could be preset to 0.5°, 1.0° or 2.0° as viewed from 145 cm. The stimulus square was superposed on a circular, 12° diameter adapting background of luminance 14 cd m$^{-2}$ and the same color (green) as the square. The device of the invention utilized in the test contained a size-perturbing circuit that caused the square's size to vary unpredictably. FIG. 1a illustrates how the square started to (say) increase its size at a fixed preset rate $\dot{a}$ deg sec$^{-1}$ (where $\dot{a}/2$ deg sec$^{-1}$ was the angular velocity of any one edge). After an unpredictable pseudo-randomized interval ($\tau$ sec), the square abruptly started to decrease in size at the same rate $\dot{a}$ deg sec$^{-1}$, and after a further unpredictable interval the square abruptly started to increase in size at the same rate. In early experiments the interval was never less than 0.4 sec and never more than 3.7 sec and had a mean value of 0.93 sec. In later experiments the limits were 1.2 sec and 12.4 sec and the mean value was 3.0 sec. The histogram of FIG. 2 shows the distribution of time intervals when the limits of $\tau$ were set at 0.4 sec and 3.7 sec.

The subject's task was to maintain the size of the stimulus square constant by adjusting his control knob.

Figure 1B:
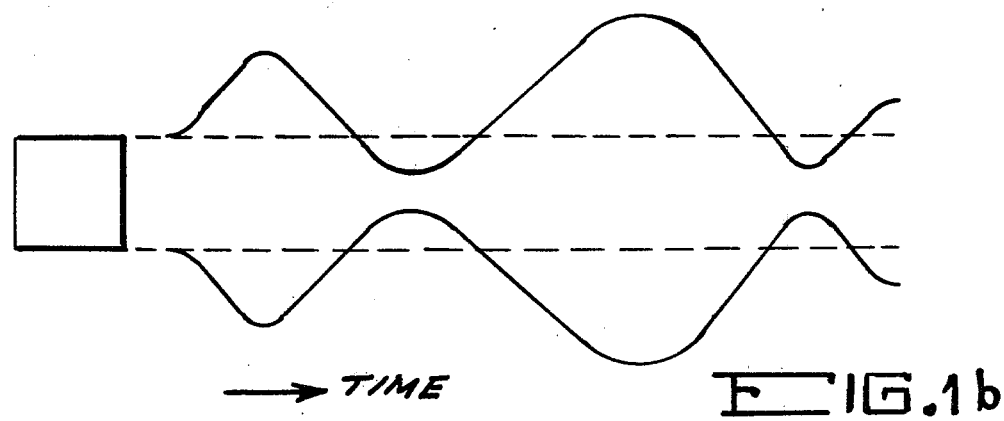
FIG. 1b illustrates the subject's antiphase response.
Figure 1C:
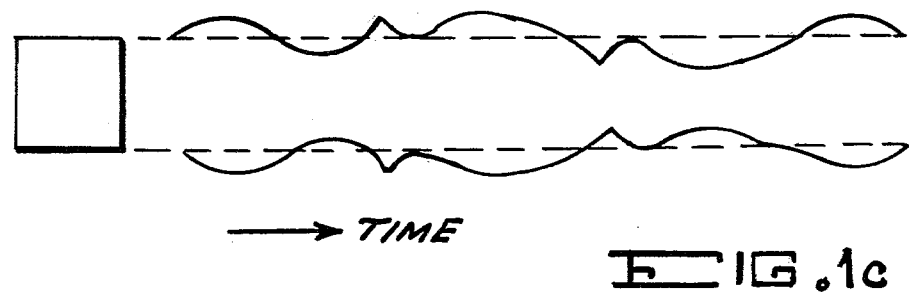
FIG. 1c illustrates the subject's tracking error plotted versus time.

There were two alternative ways in which the subject's knob could control the stimulus size. At the start of the experiment one or other of these tracking modes was selected. In the first tracking mode, a given position of the subject's control knob produced a unique rate of change of size ($\dot{a}$ deg sec$^{-1}$). Thus, the square's size would remain constant if the subject set his control knob to a position that exactly cancelled the rate of change of square size caused by the size-perturbing circuit. When, at an unpredictable instant, the direction of changing-size abruptly reversed, the subject attempted to respond as quickly as possible by resetting his control knob to a new position. FIG. 1b is an (idealized) illustration of the signal generated by the subject in his attempt to track the unpredictable constant-velocity changing-size signal illustrated in FIG. 1a. FIG. 1b illustrates the finding that, unsurprisingly, subjects responded inaccurately to reversals that followed at very short intervals. FIG. 1c illustrates the size of tracking error obtained by subtracting the subject's tracking response of FIG. 1b from the antiphase stimulus of FIG. 1a.

The second tracking mode was that a given setting of the subject's control knob produced a unique static size of the stimulus square. In this mode the subject had to continuously rotate his control knob at a constant rate in order to cancel the constant rate of change of size of the stimulus. When, at an unpredictable instant, the direction of the changing size abruptly reversed, the subject attempted to respond as quickly as possible by reversing the direction of rotation of his control knob.

Several measures of tracking error were available as follows: (a) a continuous analogue output proportional to the instantaneous error of square size; (b) a continuous analogue output proportional to the instantaneous error in the rate of change of square size; (c) the integral over the test interval of RMS error filtered from DC to 0.25 Hz; (d) the integral over the test interval of RMS error filtered from 0.25 Hz to 0.75 Hz; (e) the integral over the test interval of RMS error filtered from 0.75 Hz upwards; (f) the difference in absolute size between the start and the end of the test interval.

Provision was made to select at the start of the test interval whether the RMS error measured in (c), (d) and (e) above was size error or rate of change of size error. The test interval could be preset at 30 sec, 60 sec, or 120 sec by means of a switch.

A second stage of the test procedure consisted of tracking noisy variations of size. One device contained a size-perturbing circuit that varied the absolute size of the square with a noisy waveform. (Note that in this mode of operation the rate of change of size was not constant. It varied with a noisy waveform also.) The bandwidth of the noise could be preset by means of switches. The lower cutoff frequency could be set to DC or 0.25 Hz, and the upper cutoff frequency could be set to 0.25, 0.5, 1.0, 2.0, 4.0 or 8.0 Hz.

When this option was selected only one tracking mode, namely control of size, was possible. Error readouts were as described above.

Figure 3A:
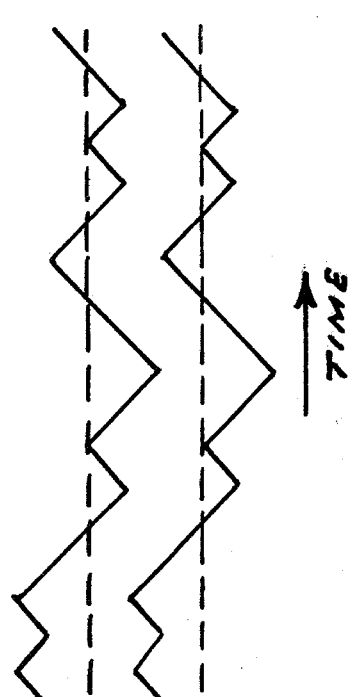
FIG. 3a illustrates constant velocity perturbations of the rate of change of position of the tracking stimulus.
Figure 3B:
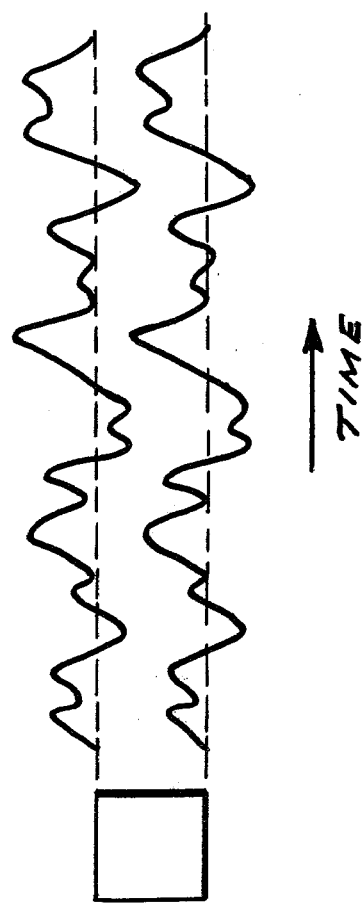
FIG. 3b illustrates noisy perturbations of the position of tracking stimulus.

A third stage of testing comprised tracking size variations in the presence of added perturbations of stimulus location and/or stimulus luminance. Any of the antiphase tracking procedures described above could be carried out in the presence of a preset amount of added inphase (sideways) motion. Two types of inphase perturbation could be added. FIG. 3a illustrates constant velocity inphase perturbation. The pseudo-randomized reversal points could be chosen either to coincide with the reversals of the antiphase tracking stimulus, or to be independent of the antiphase tracking stimulus. The velocity of the inphase stimulus could be preset. FIG. 3b illustrates a noisy inphase perturbation of the stimulus square's position. The amplitude of the inphase perturbation could be preset. The upper and lower cutoff frequencies of the noise waveform could be preset to the fixed frequencies listed above.

Stimulus luminance could also be varied by a noise waveform during tracking. This was achieved by feeding either of the two available perturbing waveforms to the intensity control of the CRT.

In addition to the above testing procedures inphase tracking is also possible. In using this approach the subject's control knob could be set to generate an inphase signal. Inphase (sideways motion) tracking, could then be carried out in several different modes as described above for antiphase tracking.

The size-tracking device of the invention consists of the several major functional parts illustrated in FIG. 4.

A rectangle (the image to be tracked) is generated on the face of cathode ray tube (CRT) 3 by the rectangle generator subsystem 4. Both the size and position of this rectangle may be controlled by the various inputs. These inputs may come from: (1) One of two identical noise generators 7 which generate bandpass-filtered "white" noise; (2) A preset-frequency sine, square or triangle wave oscillator 6; (3) One of two identical "irregular velocity reversers" 5 which generate a voltage which has a constant rate of change (velocity) but whose direction is reversed at pseudo-randomized intervals; or, (4) The subject's control potentiometer 2. The subject's control potentiometer 2 can also be fed into the irregular velocity reversers 5 so as to control the rate of change of size position of the rectangle rather than the size position of the rectangle directly.

Various error outputs are available from the rectangle generator. These outputs can be analyzed in different ways and the results displayed on digital voltmeters (DVM) 8.

An expanded functional block diagram is shown in FIGS. 5-9. Detailed circuit diagrams of the various sections are shown in FIGS. 10-25. A more complete description follows.

Figure 8:
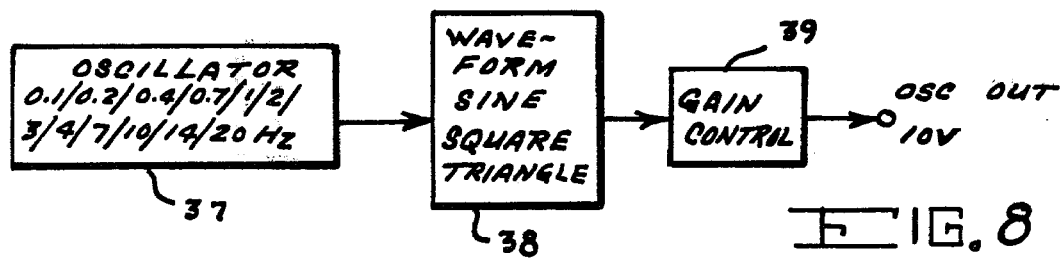
FIG. 8 is an expanded block diagram of the oscillator of FIG. 4.
Figure 9:
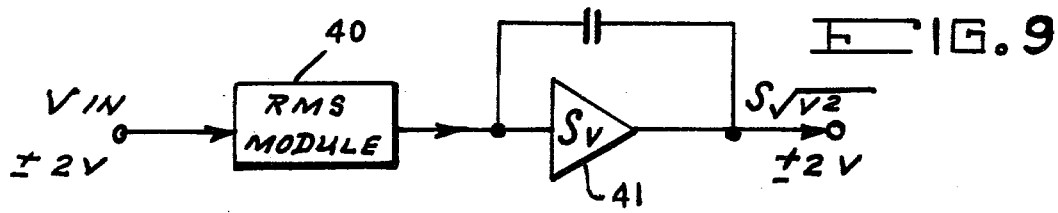
FIG. 9 is an expanded block diagram of the error analyzer of FIG. 4.
Figure 5:
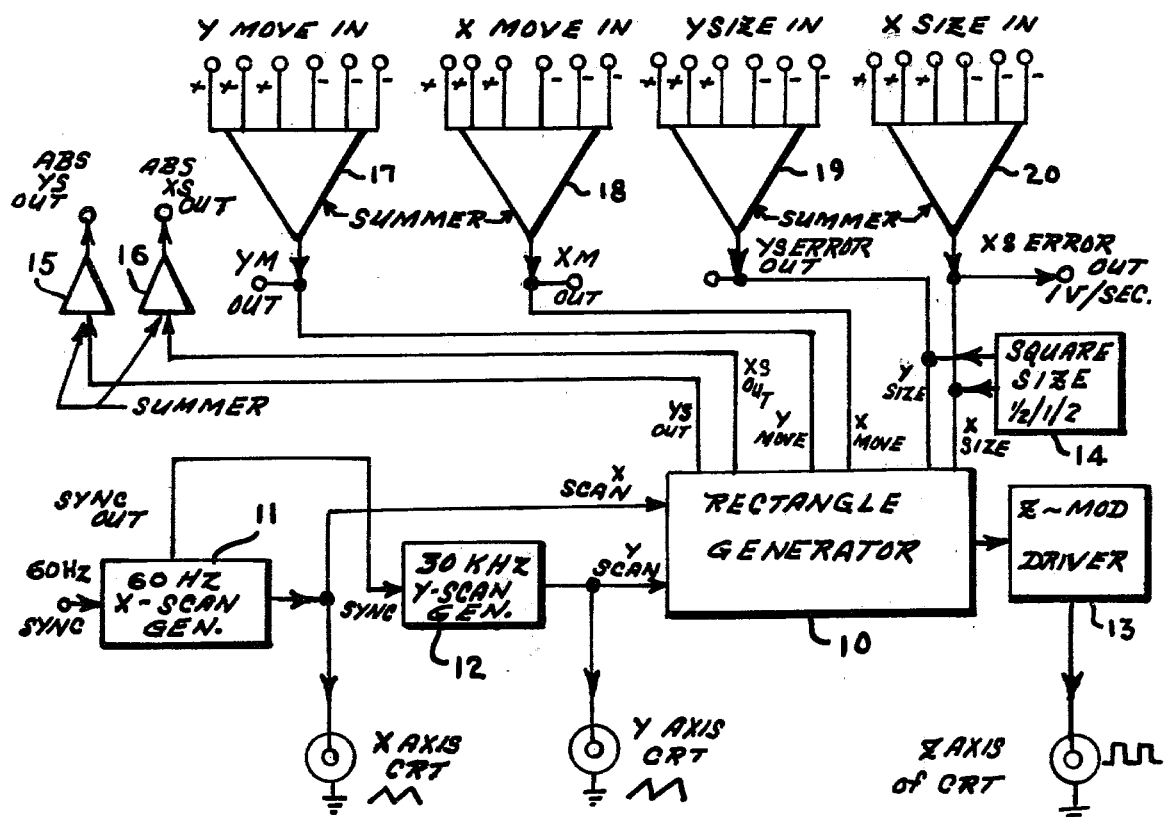
FIG. 5 is an expanded block diagram of the rectangle generator subsystem of FIG. 4.
Figure 6:
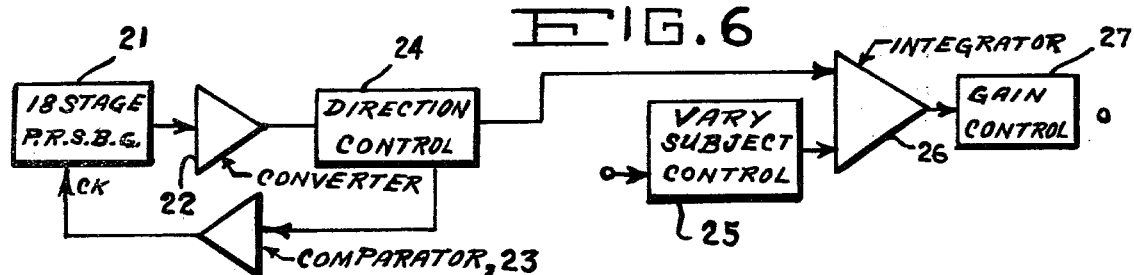
FIG. 6 is an expanded block diagram of the irregular velocity reverser of FIG. 4.
Figure 7:
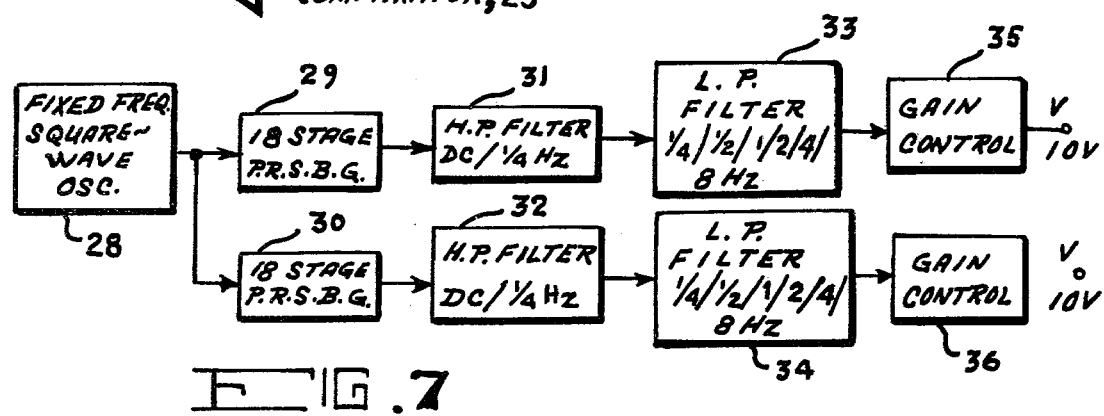
FIG. 7 is an expanded block diagram of the noise generator of FIG. 4.

FIG. 5 is described and discussed in detail below. FIG. 6 is an expanded block diagram of the irregular velocity reverser of FIG. 4. The circuit comprises pseudo-random sequence bit generator (PRSBG) 21, converter 22, direction control 24, comparator 23, vary subjects control 25, integrator 26 and gain control 27. FIG. 7 is an expanded block diagram of the noise generator of FIG. 4 and comprises fixed frequency square wave oscillator 28, PRSBG's 29, 30, high pass filters 31, 32, low pass filters 33, 34 and gain controls 35, 36. FIG. 8 is an expanded block diagram of the oscillator of FIG. 4 and comprises oscillator 37, waveform circuit 38 and gain control 39. The error analyzer of FIG. 4 is shown in expanded block diagram form in FIG. 9 and consists of RMS module 40 and integrating amplifier 41.

Figure 10:
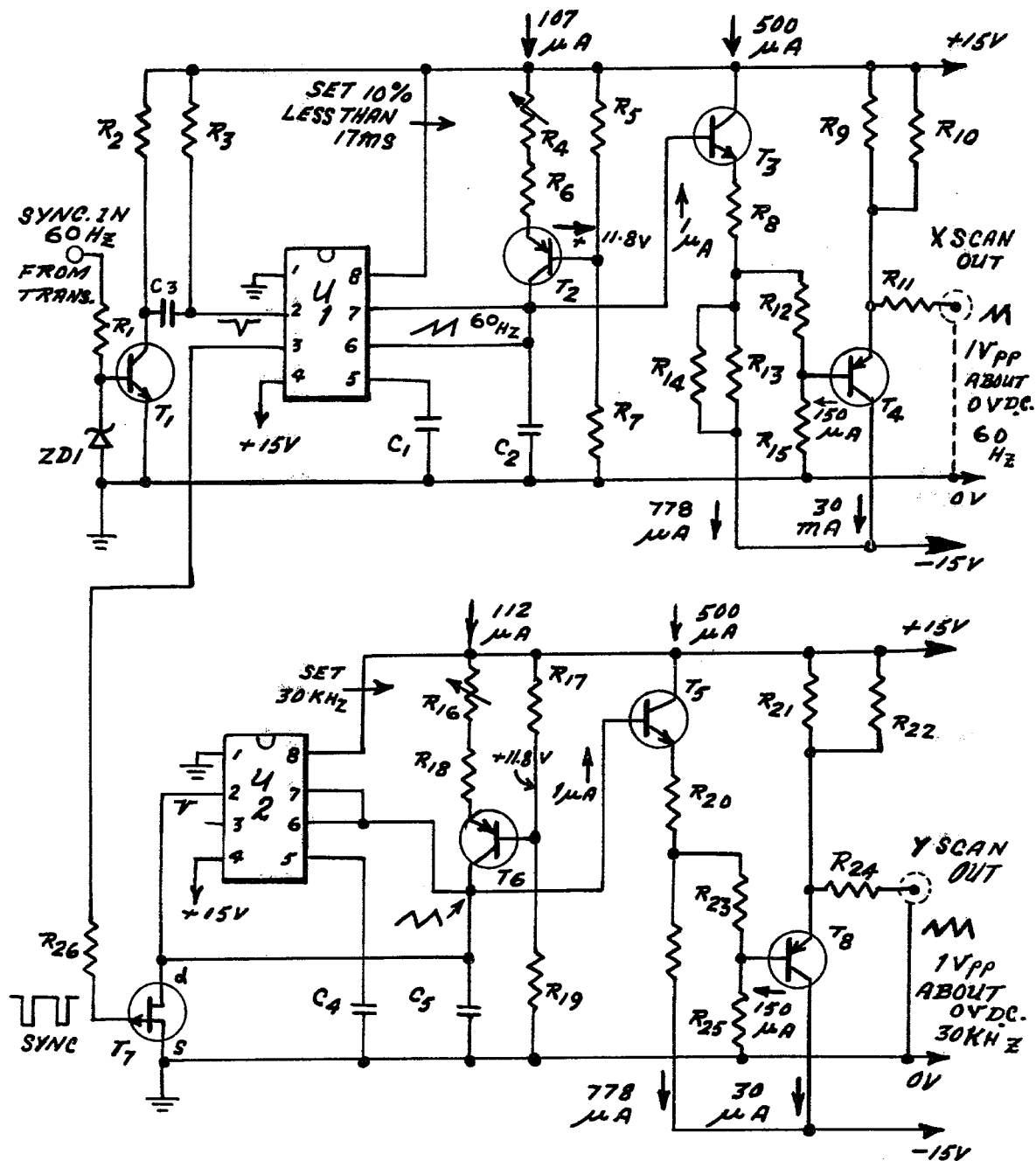
FIG. 10 is a schematic diagram of the system raster generator.

Referring to FIG. 5, the rectangle generator subsystem consists of X and Y raster generators 11, 12 the rectangle generator 10, the Z mod driver 13, and various summers 15-20. The raster generators are shown by FIG. 10 and comprise time units U1 (555), U2 (555), zener diode ZD1, transistors T1(2N3704), T2(2N906), T3(2N5057), T4(2N2909A), T5(2N5039), T6(2N3906), T7(E271), T8(2N2905A), capacitors CL–C5 and resistors R1–R25 connected in the circuit arrangements shown. The rectangle generator is shown schematically by FIG. 11 and comprises amplifier A1, A2, A4, A5(LM307), A3, A6(LM318), A7, A8, A9, A10(LM311) capacitors C6–C11, diodes D1, D2, switch S1, and resistors R26–R64. The Z mod driver is shown schematically by FIG. 12 and comprises logic unit U3(7805) capacitor C13, transistor T9(2N5772), T10(2N5772) and resistor R65–R67.

These circuits operate as follows: a 60 Hz ramp, synchronized to the local line frequency, is applied to the X plates of the CRT (FIG. 10). A 30 KHz ramp, synchronized to the X ramp, is applied to the Y plates of the CRT. This results in a uniform raster of about 500 lines covering the whole face of the CRT.

Figure 11:
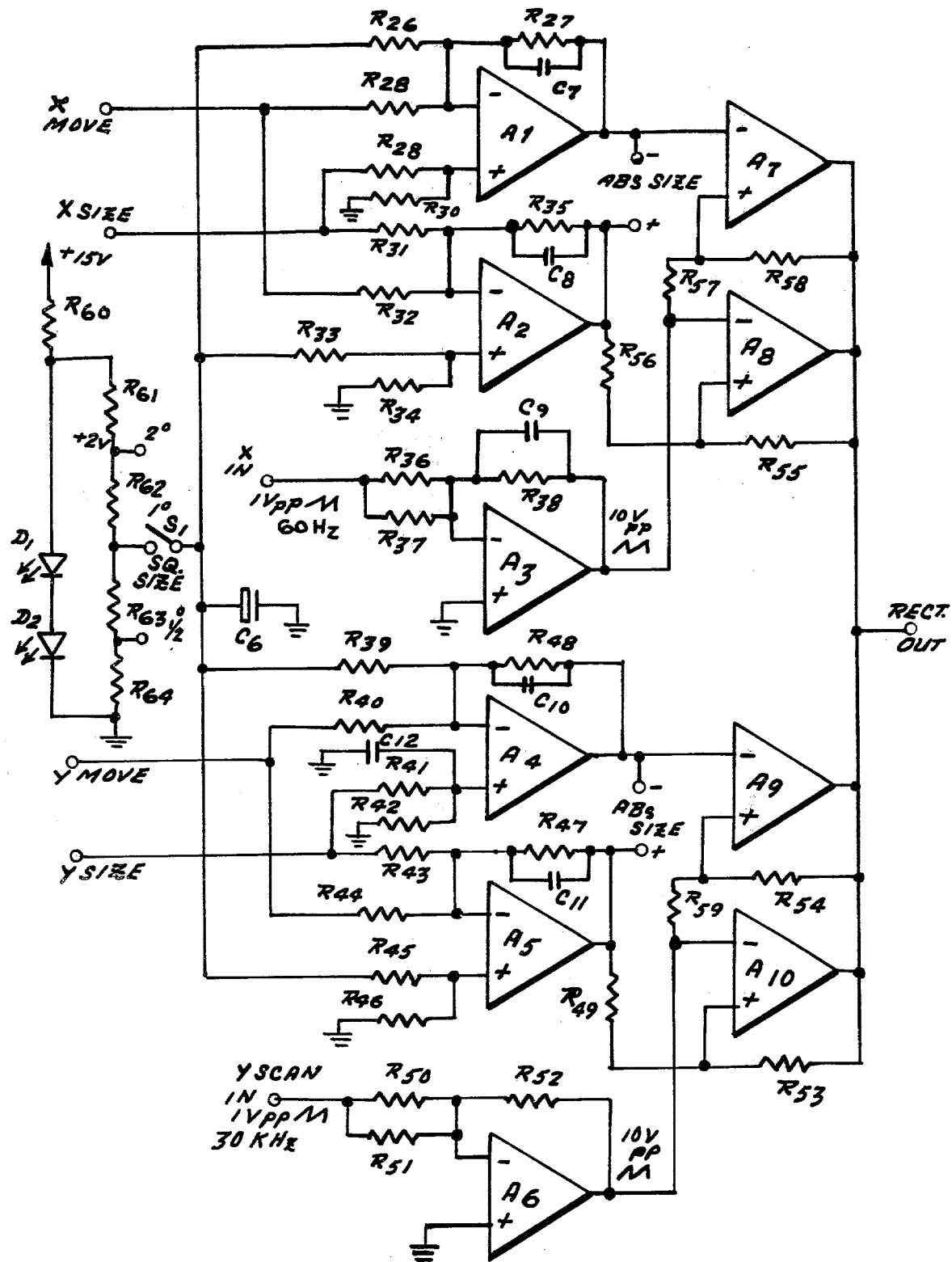
FIG. 11 is a schematic diagram of the system rectangle generator.
Figure 12:
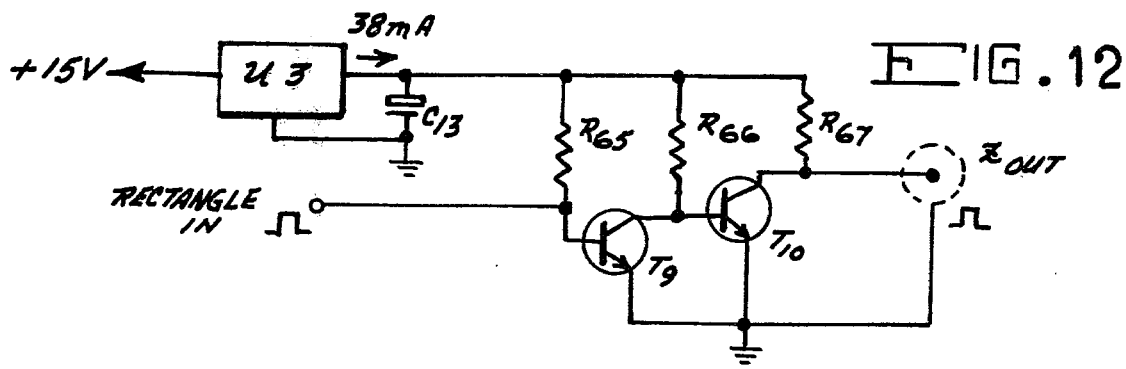
FIG. 12 is a schematic diagram of the system modulator.

The X and Y ramps are also fed to separate pairs of voltage comparators connected as "window" comparators (FIG. 11). These produce a positive output voltage, if and only if, the input (X or Y ramp) voltage lies between two predetermined voltages. The outputs of these window comparators are "logically OR-ed" and this output is fed to the Z input of the CRT via a buffer amplifier (FIG. 12).

The result is that the screen of the CRT is brightened only when both the X and Y raster voltages lie between independent predetermined limits (i.e., a bright rectangle is generated). A crucial point is that the size and position in both the X and Y directions can be varied by varying the predetermined comparison voltages—varying these voltages in opposite directions at any instant will vary the size of the rectangle; varying these voltages in the same direction at any instant will vary the position of the rectangle. Independent X size, Y size, X move and Y move inputs are provided by appropriately connected differential op-amps (FIG. 5). An extra input provides for a square of fixed size to be generated in the absence of any external input.

Figure 13:
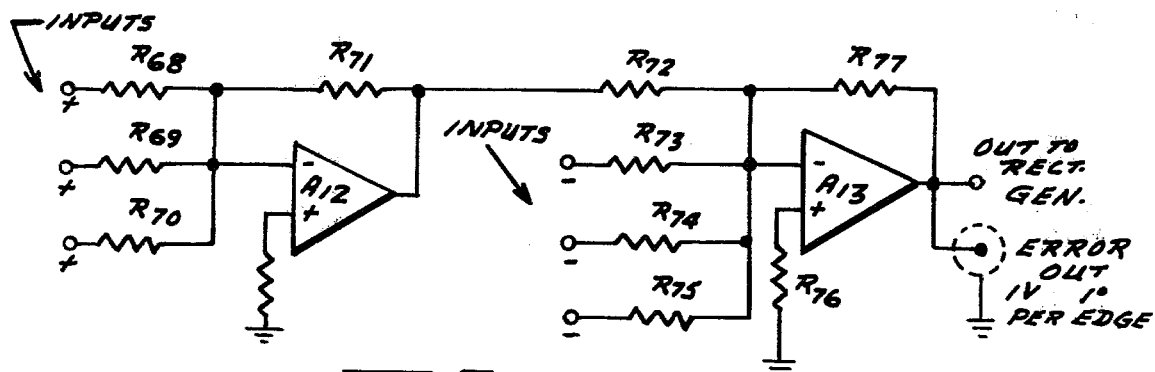
FIG. 13 is a schematic diagram of the image position movement summers of FIG. 5.
Figure 14:
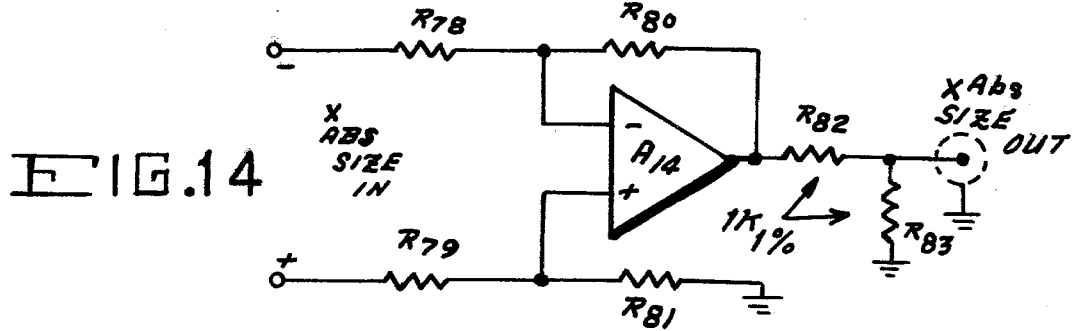
FIG. 14 is a schematic diagram of output summers of FIG. 5.
Figure 15:
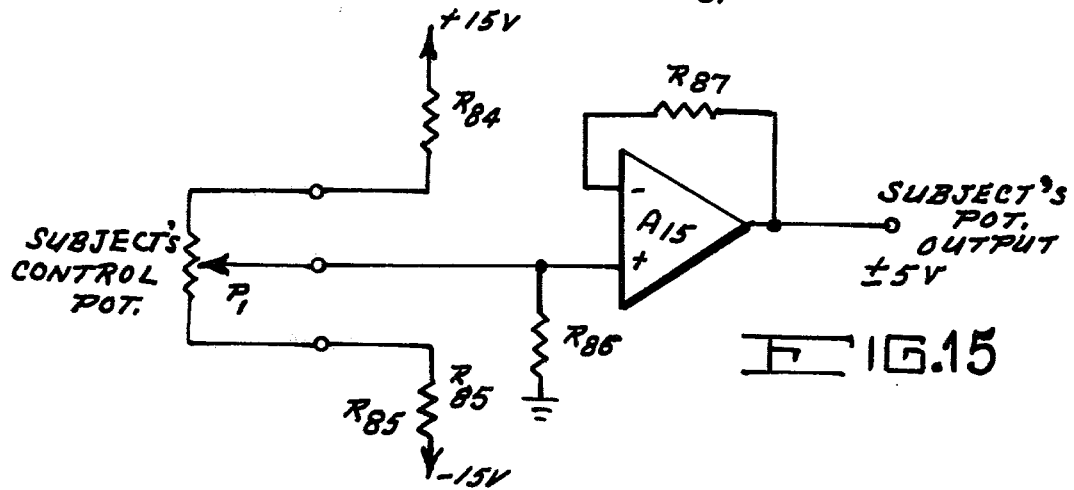
FIG. 15 is a schematic diagram of the subject's control circuit.

To enable the direct connection of several different signals to each of the four inputs of the rectangle generator, differential summers are used. Four of these are required as indicated by items 17–20 of FIG. 5. A schematic diagram of such a circuit is shown by FIG. 13. The circuit for each summer comprises amplifiers A12, A13 (LM307) and resistors R68–R77. FIG. 14 shows the schematic for summers 15, 16 of FIG. 5. This circuit comprises amplifier A14 (LM307) and resistors R78–R83.

Reference is now made to the sources of the signals used to modulate the size and position of the rectangle.

Figure 16:
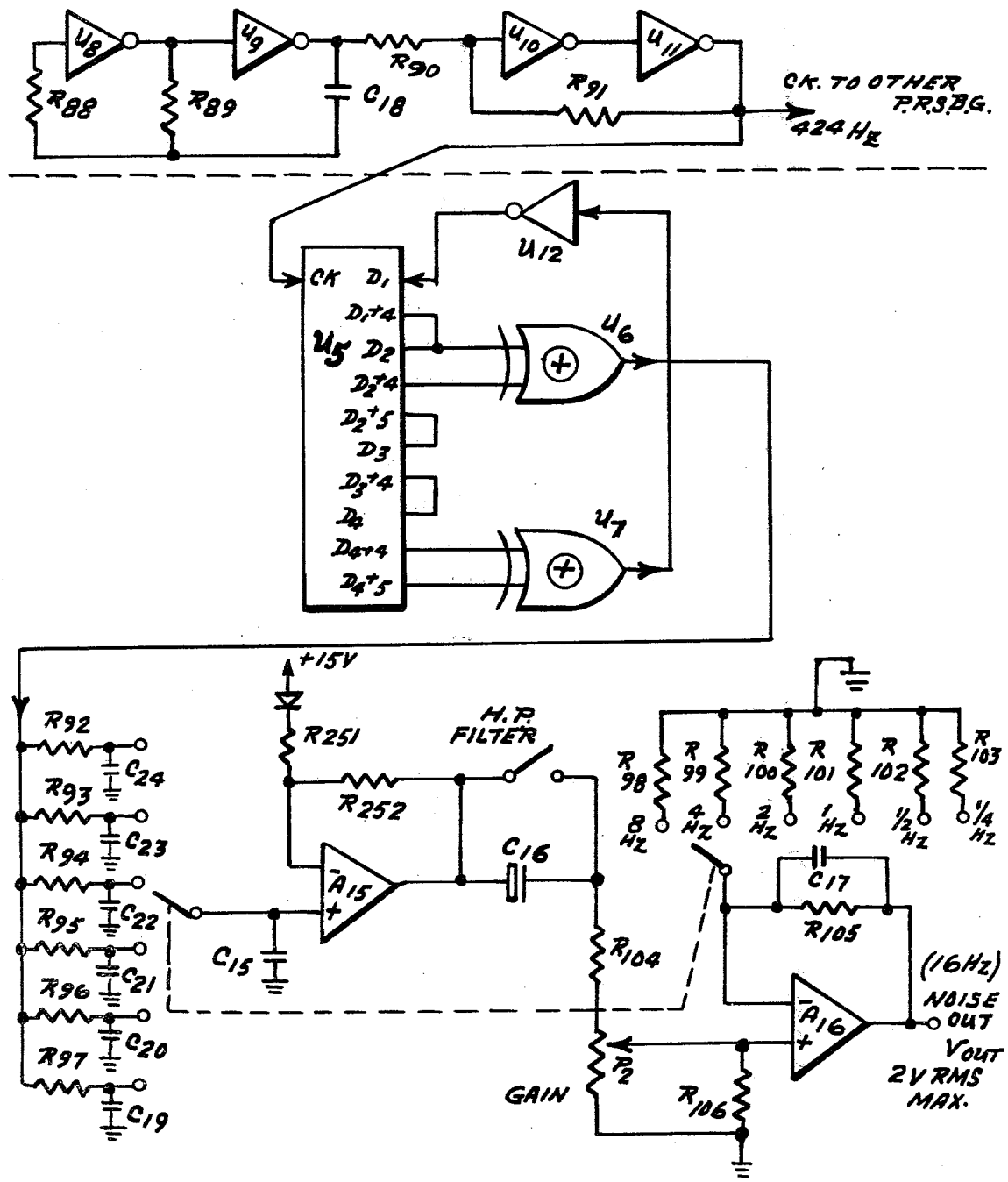
FIG. 16 is a schematic diagram of the noise generator of FIG. 4.
Figure 17:
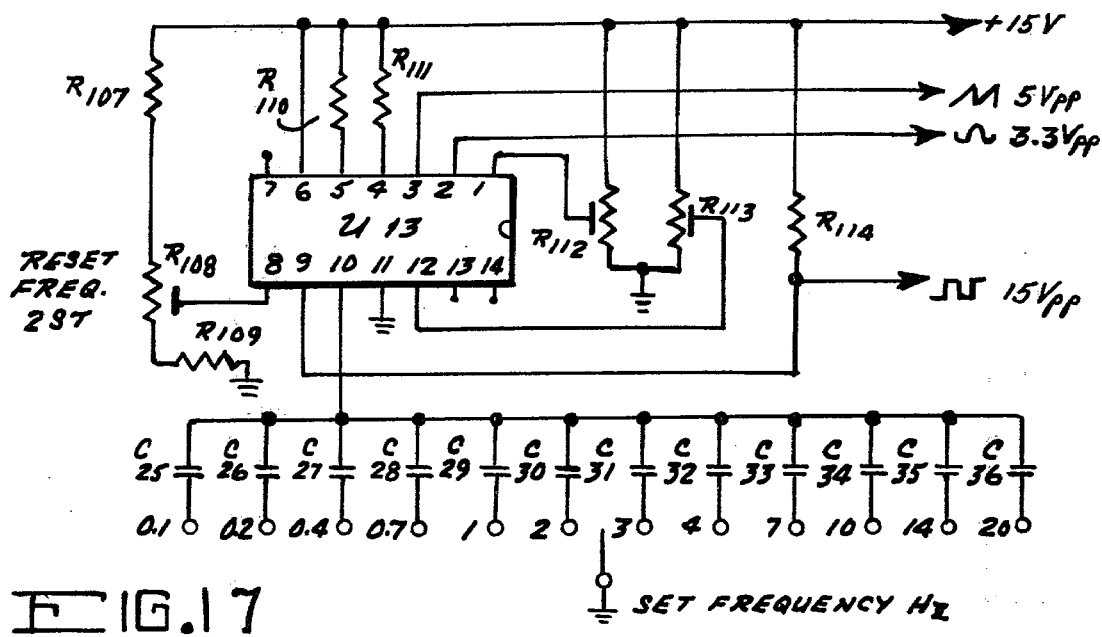
FIGS. 17 and 18 comprise a schematic diagram of the oscillator of FIG. 4.
Figure 18:
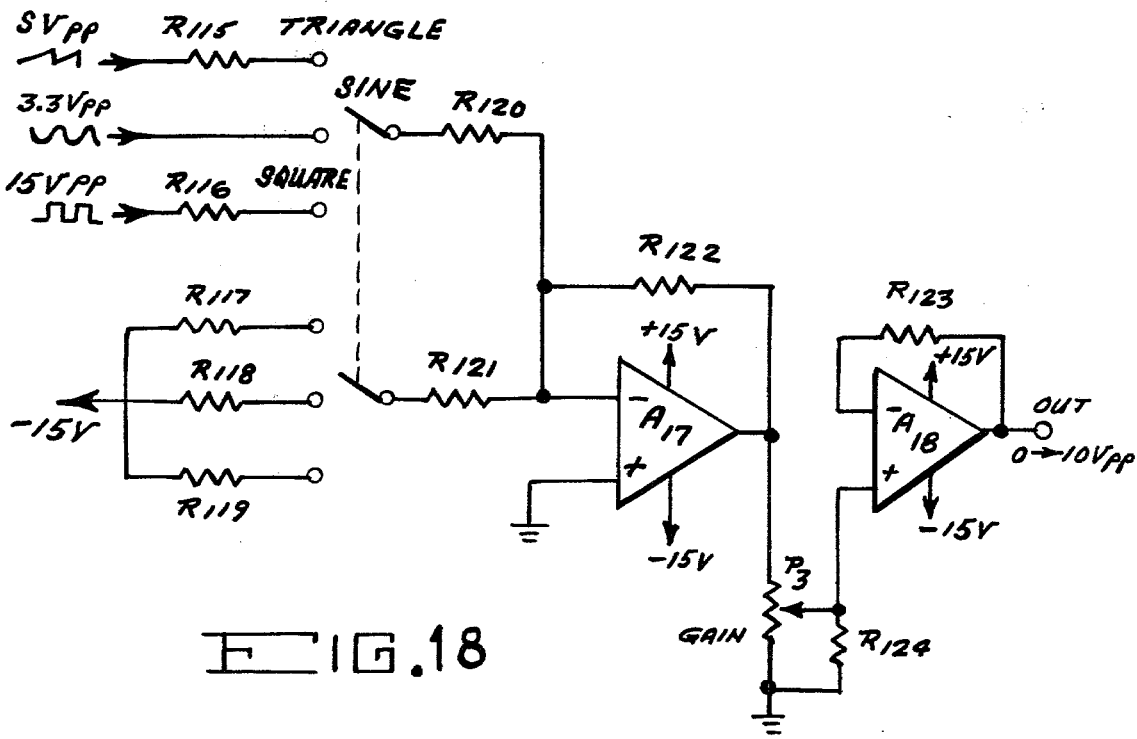
Figure 19:
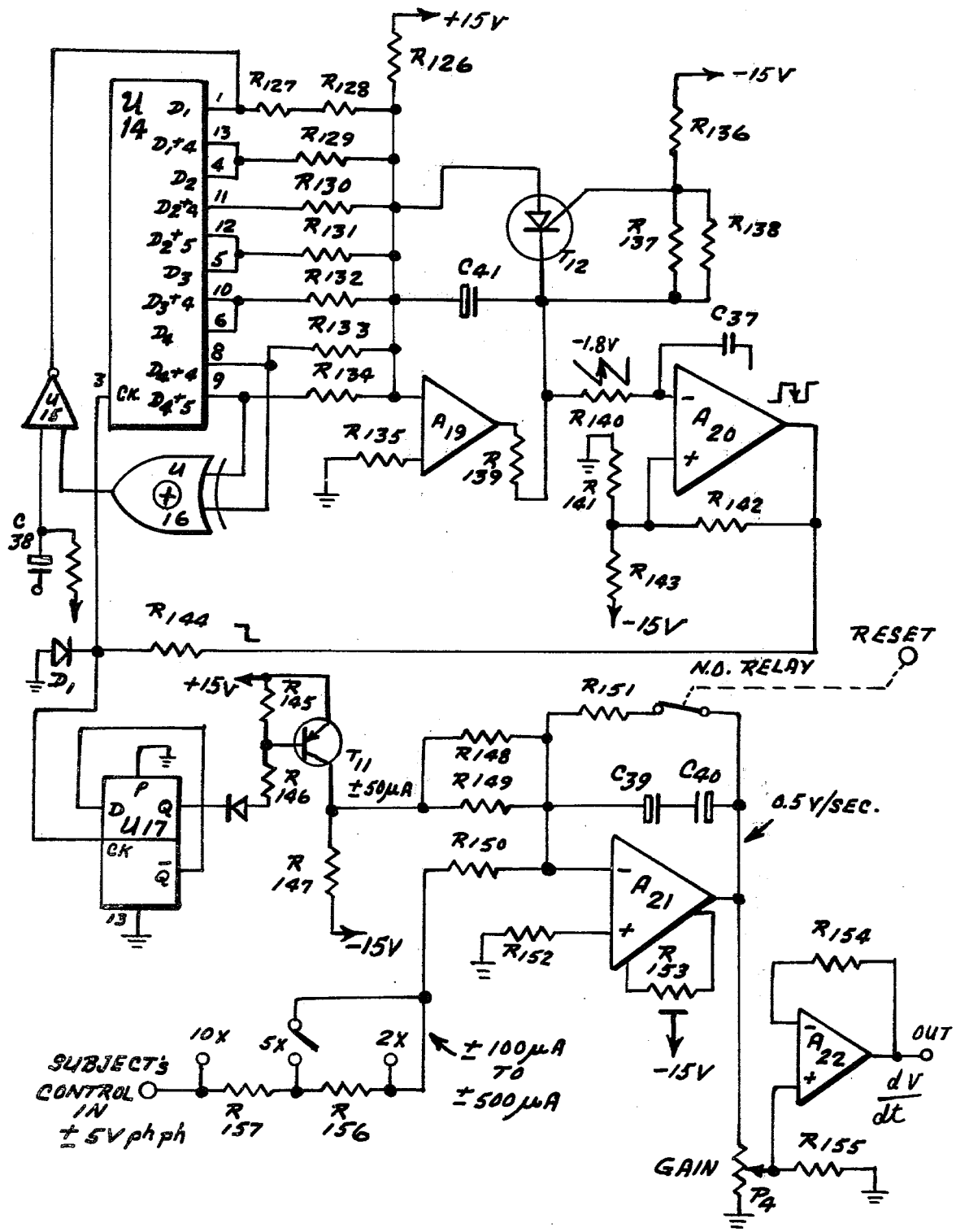
FIG. 19 is a schematic diagram of the irregular velocity reverser of FIG. 4.

First, there are two identical noise generators. These consist of pseudo-random sequence bit generators (PRSBG) built from 18 stage shift registers and clocked at about 400 Hz. (10 minute cycle time). The digital output is passed through a two-stage low-pass filter (0.18 to 5.6 Hz) and optionally through a single-stage high pass filter (0.25 Hz) to generate essentially "white" noise within a specific frequency band. A schematic diagram of this circuit is shown by FIG. 16. The noise generators each comprise exclusive OR gates U6, U7 (CD4070), PRSBG unit U5, inverter U8–U12, amplifier A15 (CA3140T), capacitors C15–C24, and resistors R88–R106.

Secondly, there is provided a preset frequency (0.1 to 20 Hz) sine, square or triangle wave oscillator. This is shown schematically in FIGS. 17 and 18 and comprises logic unit U13 (8038), amplifier A17 (CA3140T), A18 (LM 307), capacitors C25–C36, and resistors R107–R123.

Thirdly, and most importantly there are two identical irregular velocity reversers. These are illustrated schematically by FIG. 19 and comprise exclusive OR gate U16 (CD4070), logic unit U17 (CO4013), amplifiers A19, A21 (CA3140T), A20, A22 (LM307), PRSBG unit U14, capacitors C37–C41, potentiometer P4 and resistors R126–R157. These circuits generate a voltage which has a constant rate of change (velocity) but whose direction of change is reversed at pseudo-randomized intervals as follows. A number (in this case seven) of outputs from an 18 stage PRSBG control different currents which are summed, together with a fixed current, and used to charge an integration capacitor. When the voltage across this capacitor exceeds a preset level the capacitor is discharged. This discharge pulse is used to clock the PRSBG, causing the control bits for the individual currents to change and hence produce a new integration current. The interval between clock pulses thus depends on the output bits from the PRSBG and since these vary pseudo-randomly, so does the inter-pulse interval. These clock pulses are used to switch the input to a second integrator between equal positive and negative voltages thus controlling the direction of change of the output voltage but leaving unaffected the rate of change.

Finally there is produced the subject's control which is simply a potentiometer generating a voltage. This circuit is shown schematically in FIG. 15 and comprises amplifier A15 (LM307), potentiometer P1, and resistors R84–R87.

In order to control the rate of change of sie position of the rectangle, rather than its size position directly, the output from the subject's control can be fed into the second integrator of the irregular velocity reverser.

Six error outputs are available from the rectangle generator. The four inputs to the rectangle generator—X size, Y size, X move and Y move are also error outputs since any voltage at these points will constitute a deviation from the starting conditions. Two more error outputs are supplied by differential op-amps which compute the actual X and Y sizes of the displayed rectangle as shown in FIG. 14.

Figure 20:
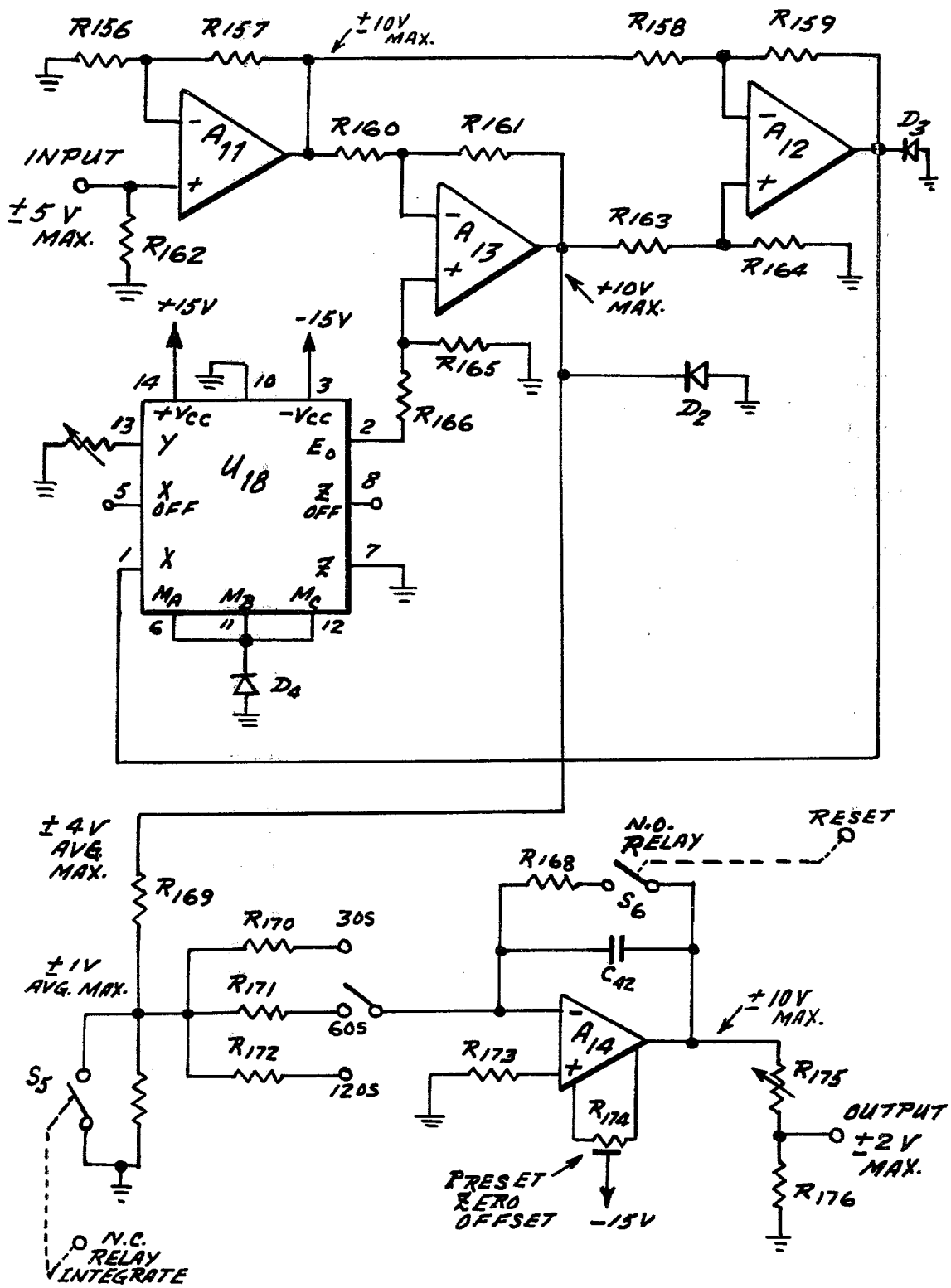
FIG. 20 is a schematic diagram of system RMS integrators.
Figure 21:
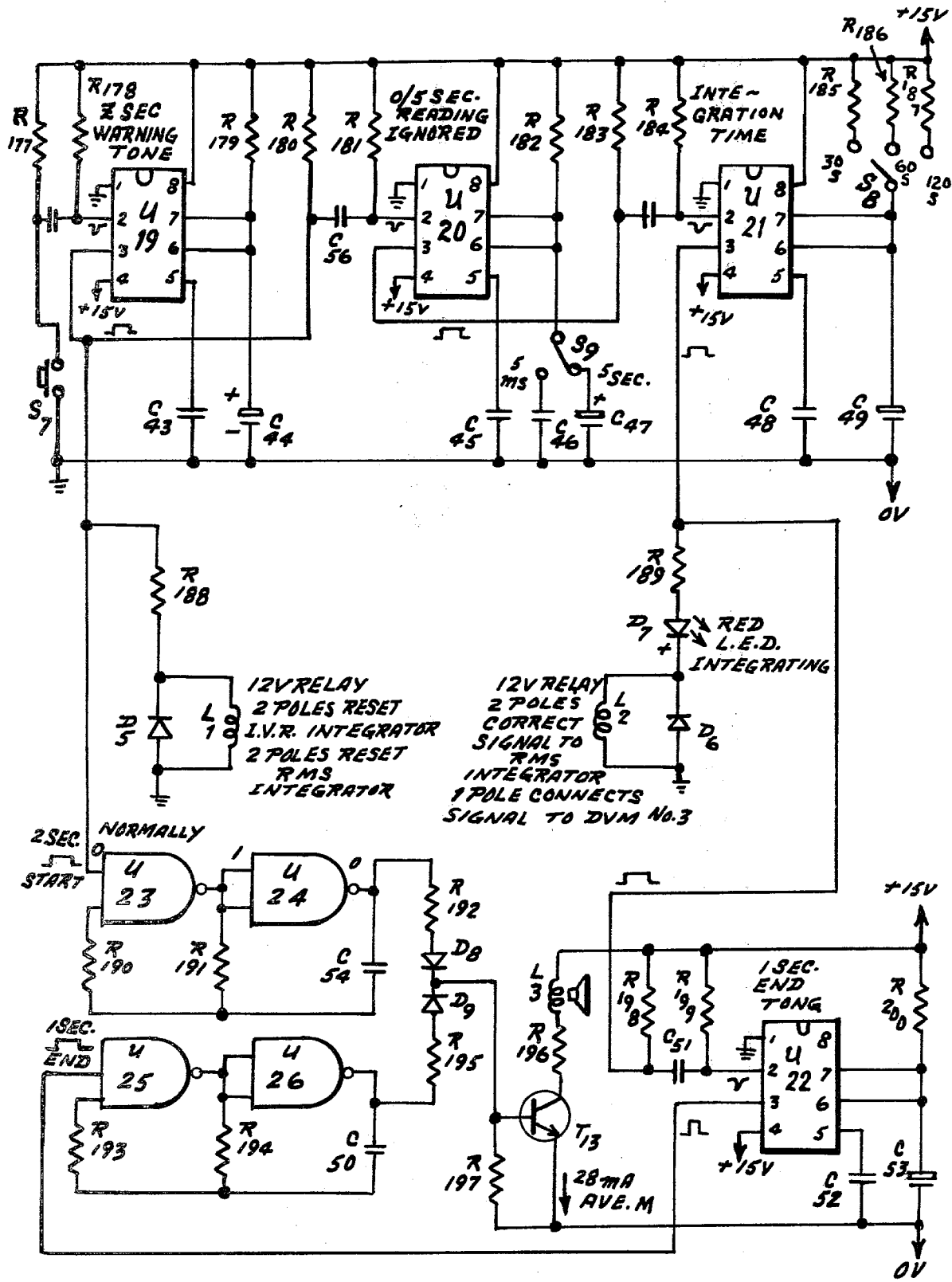
FIG. 21 is a schematic diagram of the system timing circuits.

The error analyzer consists of several parts which can be interconnected as desired. The most important part consists of a root mean square (RMS) stage followed by an integrator. The circuit is shown by FIG. 20 and comprises logic unit U18 (Burr Brown 4302), amplifiers A11–A13 (LM307) A14(CA3140), switches S5, S6, diodes D2–D4 (IN914), and resistors R156–R176. This enables the integrated RMS error over a period of time to be computed. Two of these were available and later a third was added. The outputs from these integrators are displayed on three DVM's. The integration period is controlled by a sequence of timers. The timer circuit is shown by FIG. 21 and comprises timers U19–U22 (555), NAND gates U23–U26 (DC4011), diodes D6, D7, D8, D9, switches 57, 58, 59, transistor T13 (2N3904), inductances L1, L2, capacitors C43–C57 and resistors R177–R200. When initiated, a two second audible warning tone is produced during which the various integrators are reset. This is followed by an (optional) five second delay when no integration takes place; this allows for the experimental subject's starting errors. This is followed by the integration period (typically 60 sec) during which the RMS errors made by the subject are integrated. Finally a one second tone signals the end of an experimental run. The final integrated errors can then be read from the DVM's.

Figure 22:
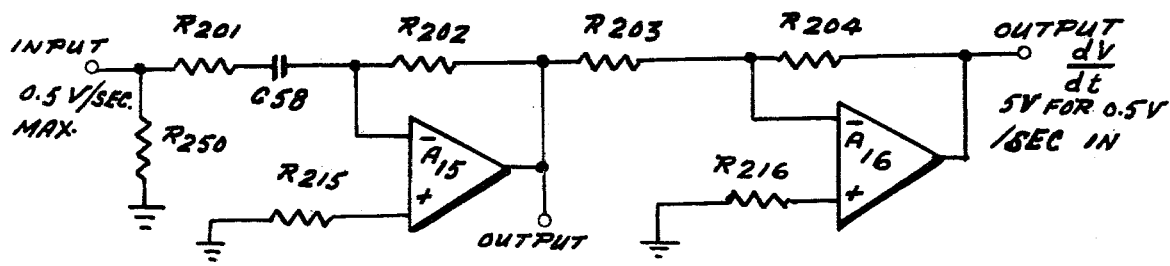
FIG. 22 is a schematic diagram of system velocity error computing differentiators.

Two differentiators enable velocity errors (as opposed to position/size errors) to be computed. The circuit for the differentiator is shown in FIG. 22 and comprises amplifiers A15, A16 (LM307), capacitor C58, and resistors R201, R215, R216 and R250.

Figure 23:
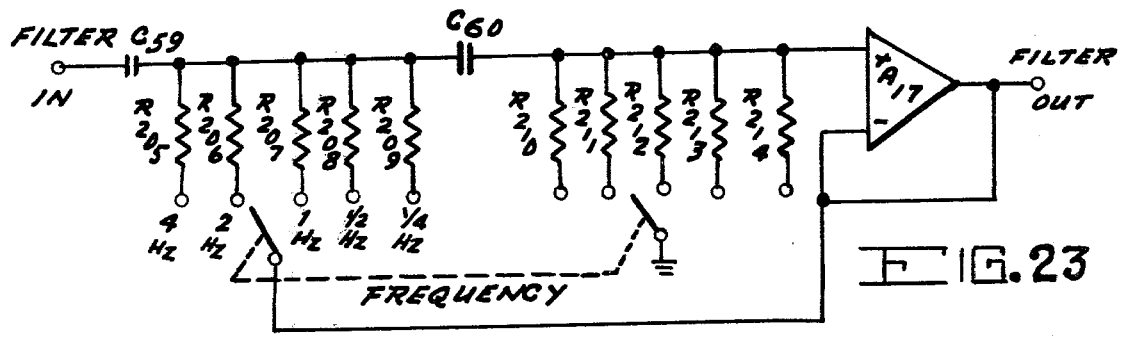
FIG. 23 is a schematic diagram of a system high pass filter.
Figure 24:
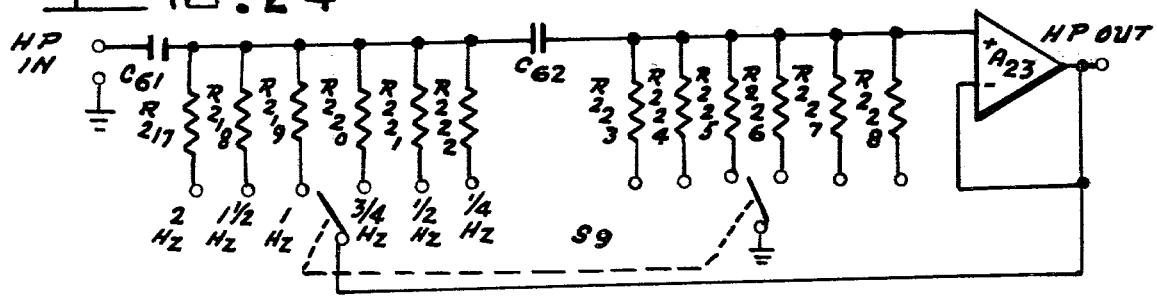
FIG. 24 is a schematic diagram of a second system high pass filter.
Figure 25:
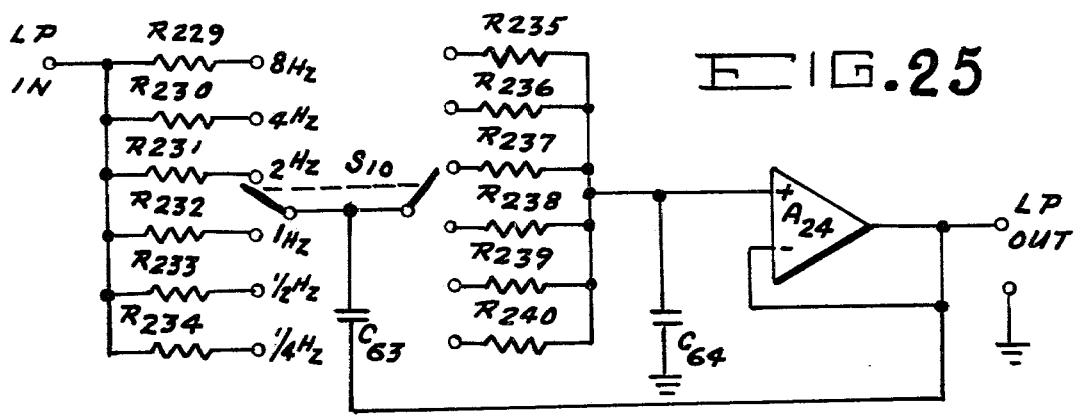
FIG. 25 is a schematic diagram of a system low pass filter.

A first preset frequency (0.25 to 4 Hz) high pass filter, a second high pass filter and a low pass filter are provided for enabling errors in specific frequency bands to be computed. The first high pass filter is shown in FIG. 23 and comprises amplifier A17 (CA3140), capacitor C59 and resistors R205-R214. The second high pass filter is shown in FIG. 24 and comprises amplifier A23 (CA3140) capacitors C61, C62, and resistors R217-R228. The low pass filter is shown in FIG. 25 and comprises amplifier A24 (CA3140), switch S10, capacitor C63, and resistors R229-R240.

The whole apparatus is powered by a conventional power supply (not shown).

While the invention has been described in one presently preferred embodiment it is understood that the words which have been used are words of description rather than words of limitation and that changes within the purview of the appended claims may be made without departing from the scope and spirit of the invention in its broader aspects.

What is claimed is:

1. The method of measuring a person's hand-eye coordination in tracking a changing-size image comprising the steps of
    generating an image on a screen within the view of a person being tested,
    varying the size of said image,
    providing tracking means whereby said person, as a test procedure, tracks the changes in size of said image by effecting cancellation of image size change, and
    comparing the resultant tracking response with image size change whereby the difference therebetween provides a measure of the person's hand-eye coordination.

2. The method of measuring a person's hand-eye coordination defined in claim 1 including the step of simultaneously laterally moving said image.

3. The method of measuring a person's hand-eye coordination defined in claim 2 including the step of varying the relative intensity of said image and said screen.

4. The method of measuring a person's hand-eye coordination defined in claim 1 wherein the size of said image is varied at a constant rate of change.

5. The method of measuring a person's hand-eye coordination defined in claim 4 wherein the size of said image is alternately increased and decreased in a random manner.

6. The method of measuring a person's hand-eye coordination defined in claim 1 wherein the size of said image is varied as a function of a noisy waveform.

7. The method of measuring a person's hand-eye coordination defined in claim 2 wherein the lateral movement of said image is of constant velocity.

8. The method of measuring a person's hand-eye coordination defined in claim 2 wherein the lateral movement of said image is a function of a noisy waveform.

9. Apparatus for measuring a person's hand-eye coordination in tracking a changing-size image comprising
    a cathod ray tube having a screen and X scan, Y scan and intensity inputs,
    an image figure generator subsystem,
    a first, programmable image figure size control circuit generating a first image figure size control signal,
    a second image figure size control circuit responsive to manual control means and generating a second image figure size control signal, said image figure generator subsystem functioning in response to said first and second image figure size control signals and feeding its outputs to said cathode ray tube X scan, Y scan and intensity inputs to generate an image on the screen thereof, and whereby tracking of a changing-size image is achieved by manipulating said manual control means to cause said second image size control signal to cancel the effects of said first image size control signal.

10. Apparatus for measuring a person's hand-eye coordination in tracking a changing-size image as defined in claim 9 including means for processing said first and second image figure size control signals to provide output signals that are a measure of tracking error.

11. Apparatus for measuring a person's hand-eye coordination in tracking a changing-size image as defined in claim 10 including an image lateral displacement circuit generating image displacement control signals feeding said rectangle generator subsystem and controlling the outputs thereof in response to said image displacement control signals.

12. Apparatus for measuring a person's hand-eye coordination in tracking a changing-size image as defined in claim 11 wherein said first programmable image figure size control circuit comprises an oscillator circuit.

13. Apparatus for measuring a person's hand-eye coordination in tracking a changing-size image as defined in claim 11 wherein said first prorammable image figure size control circuit comprises a noise generator.

14. Apparatus for measuring a person's hand-eye coordination in tracking a changing-size image as defined in claim 11 wherein said first programmable image figure size control circuit comprises an irregular velocity reverser circuit.

15. Apparatus for measuring a person's hand-eye coordination in tracking a changing-size image as defined in claim 11 wherein said first programmable image figure size control circuit comprises an oscillator circuit, a noise generator and an irregular velocity reverser circuit, said circuits being selectively integrated into said rectangle generator subsystem.

16. Apparatus for measuring a person's hand-eye coordination in tracking a changing-size image as defined in claim 15 wherein said second image figure size control circuit comprises a manually operated potentiometer circuit feeding said rectangle generator subsystem and controlling the effect of said first image figure size control signal.

17. Apparatus for measuring a person's hand-eye coordination in tracking a changing-size image as defined in claim 16 wherein said rectangle generator subsystem comprises
    a rectangle generator circuit receiving inputs from said image lateral displacement circuit and said first programmable image figure size control circuit and feeding said cathode ray tube inputs,
    an X scan generator feeding said rectangle generator circuits and the X axis circuit of said cathode ray tube, a Y scan generator feeding said rectangle generator circuit and the Y axis circuit of said cathode ray tube, and a Z modulator driver receiving an input from said rectangle generator circuit and feeding the intensity input of said cathode ray tube.

18. Apparatus for measuring a person's hand-eye coordination in tracking a changing-size image as defined in claim 17 wherein said means for processing first and second image size control signals comprises an error analysis circuit.

19. Apparatus for measuring a person's hand-eye coordination in tracking a changing-size image as defined in claim 18 including digital voltmeter display means connected to display the outputs of said error analysis circuit.

* * * * *